US006309358B1

United States Patent
Okubo (10) Patent No.: US 6,309,358 B1
(45) Date of Patent: Oct. 30, 2001

(54) TUBE UNIT SYSTEM INCLUDING AN ADAPTER INTERPOSED BETWEEN A CONNECTOR AND A CONNECTING PART

(75) Inventor: Itaru Okubo, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/262,830

(22) Filed: Mar. 5, 1999

(30) Foreign Application Priority Data

Mar. 5, 1998 (JP) .................................................. 10-53564

(51) Int. Cl.$^7$ ........................................................ A61B 8/14
(52) U.S. Cl. ................................................................ 600/466
(58) Field of Search .................................... 600/459, 463, 600/471, 462, 466, 467, 897; 439/135; 251/149.1

(56) References Cited

U.S. PATENT DOCUMENTS

| | | |
|---|---|---|
| 4,522,196 | 6/1985 | Cunningham et al. . |
| 5,353,798 | 10/1994 | Sieben . |
| 5,401,245 * | 3/1995 | Haining ................................... 604/86 |
| 5,445,155 | 8/1995 | Sieben . |
| 5,476,107 * | 12/1995 | Oakley et al. ........................ 128/897 |
| 5,498,230 | 3/1996 | Adair . |
| 5,630,419 * | 5/1997 | Ranalletta ............................. 600/459 |
| 5,678,551 * | 10/1997 | Stevens .................................. 600/437 |

FOREIGN PATENT DOCUMENTS

| | | |
|---|---|---|
| 728444 | 8/1996 | (EP) . |
| 2148526 | 5/1985 | (GB) . |

* cited by examiner

Primary Examiner—Marvin M. Lateef
Assistant Examiner—Ali M. Imam
(74) Attorney, Agent, or Firm—Burns, Doane, Swecker & Mathis, LLP

(57) ABSTRACT

An ultrasound imaging catheter system 10 comprises an ultrasound imaging catheter 1 provided with a connector 5 positioned on the handle side thereof, an external drive device 6 provided with a connecting part 20 for connection to the connector 5 of the ultrasound imaging catheter 1, and an adapter 7 interposed between the connector 5 and the connecting part 20 and having undergone a purifying treatment such as sterilization, the adapter 7 being removable relative to the connector 5 of the ultrasound imaging catheter 1 and the connecting part 20 of the external drive device 6. The construction prevents the connector 5 part of the ultrasound imaging catheter 1 from contamination and allows it to retain a sterilized state thereof and enables the ultrasound imaging catheter 1 to be attached to and detached from the external drive device 6 without interrupting the operation.

12 Claims, 14 Drawing Sheets

TUBE UNIT SYSTEM INCLUDING AN ADAPTER INTERPOSED BETWEEN A CONNECTOR AND A CONNECTING PART

BACKGROUND OF THE INVENTION

1. Field of the Invention

This invention relates to a tube unit system such as an ultrasound imaging catheter system for displaying the sectional view of a tubular cavity or determining blood stream with the aid of an inserting part provided with a tube and inserted into the body cavity such as a blood vessel or a vein or an endoscope system for visual observation of the inside of a tubular cavity.

2. Description of the Related Art

The ultrasound imaging catheter system so adapted as to effect display of the sectional view of a tubular cavity by inserting into the body cavity a catheter provided at the leading end side of a rotary drive shaft thereof with an ultrasound transducer has been heretofore known.

This ultrasound imaging catheter system is readied for use by having a connector of the catheter in a sterilized state inserted into a connecting part of an external drive device, i.e. an unsterilized part serving to rotate the drive shaft. Once the connector is joined to the external drive device, therefore, the part of the connector brought into contact with the external drive device is fated to be contaminated. For the purpose of precluding the possibility that the operator's hands will be contaminated by the part of the connector, therefore, the connector and the external drive device which are in a connected state are not allowed to be separated from each other until the manipulation of the catheter is completed.

When the catheter is manipulated in various ways while the connector of the catheter is kept in connection with the external drive device, however, the body of machine or operator possibly rides on the connected parts of the ultrasound imaging catheter and the external drive device and, as a result, brings the problem of compelling the ultrasound imaging catheter to sustain breakage besides the possibility that the delicate operation of the catheter will be obstructed.

When the ultrasound imaging catheter is to be used, it must be first connected to the external drive device and then given a trial run intended to confirm normal operation before it is inserted into the body cavity. When the ultrasound imaging catheter in use is designed for the self-guiding operation which relies on the operator's application of torque to the catheter to produce a motion of the catheter to the neighborhood of the affected part without requiring use of a guide wire, therefore, since this catheter cannot be operated while it is kept in connection with the external drive device, the operator has no alternative but to remove the connector of the catheter from the external drive device subsequently to the confirmation of the normal operation mentioned above and then proceed to operate the catheter. As a means to prevent the operator s hands from being contaminated in this case, the method of covering the connector with a sterilized cap may be used. This method, however, has the problem of entailing a complicated work which is fated to urge deliberation.

SUMMARY OF THE INVENTION

It is an object of this invention to provide a tube unit system which, by means of a sterilized part interposed between the connector of such a tube unit as a catheter and the external unit, prevents the part of the connector from contamination and keeps intact the sterilized state of the tube unit such as the catheter and facilitate separation of the two connected parts.

One aspect of this invention is directed to a tube unit system which comprises a tube unit provided with an inserting part possessed of a tube to be inserted into a body cavity and a connector disposed on the handle side of the inserting part;

an outer unit provided with a connecting part for connection to the connector of the tube unit; and an adapter intended for interposition between the connector and the connecting part and already subjected to a purifying treatment as by sterilization, the adapter being arbitrarily attachable to and detachable from the connector and the connecting part.

In accordance with this invention, the part of the connector of the tube unit can be prevented from contamination and, as a result, the sterilized state of the tube unit can be kept intact by causing the adapter which has undergone the purifying treatment as by sterilization to be interposed between the tube unit and the external unit. Consequently, the operator while using the catheter is enabled to attach tube unit to and detach it from the external unit catheter and promote prevention of the tube unit from breakage.

Another aspect of this invention is directed to a device for protecting an article which has undergone a purifying treatment against a contaminated article, which comprises a bag already subjected to a purifying treatment as by sterilization and provided with a hole; and an adapter provided with a hollow body and a retaining part adapted to be held manually by the operator and already subjected to a purifying treatment as by sterilization;

the bag being enabled to be fixed to the adapter in such manner that the hole thereof will be located at the center of the hollow body.

Still another aspect of this invention is directed to method for visually observing the appearance of the body cavity of a given patient by means of the ultrasound imaging catheter, which method comprises a step of covering an external drive device for driving the ultrasound imaging catheter with a bag subjected to a purifying treatment as by sterilization;

a step of connecting an adapter subjected to a purifying treatment as by sterilization to the connecting part of the external drive device;

a step of connecting a connector of an ultrasound imaging catheter subjected to a purifying treatment as by sterilization through the medium of the adapter to the external drive device; and a step of setting the external drive device operating.

The objects, characteristics, and special features of this invention other than those set forth above will become apparent from the description to be given herein below with reference to preferred embodiments illustrated in the accompanying drawings.

DETAILED DESCRIPTION OF THE PREFERRED EMBODIMENT

The embodiments of this invention will be described below with reference to the accompanying drawings.

Figure 1:
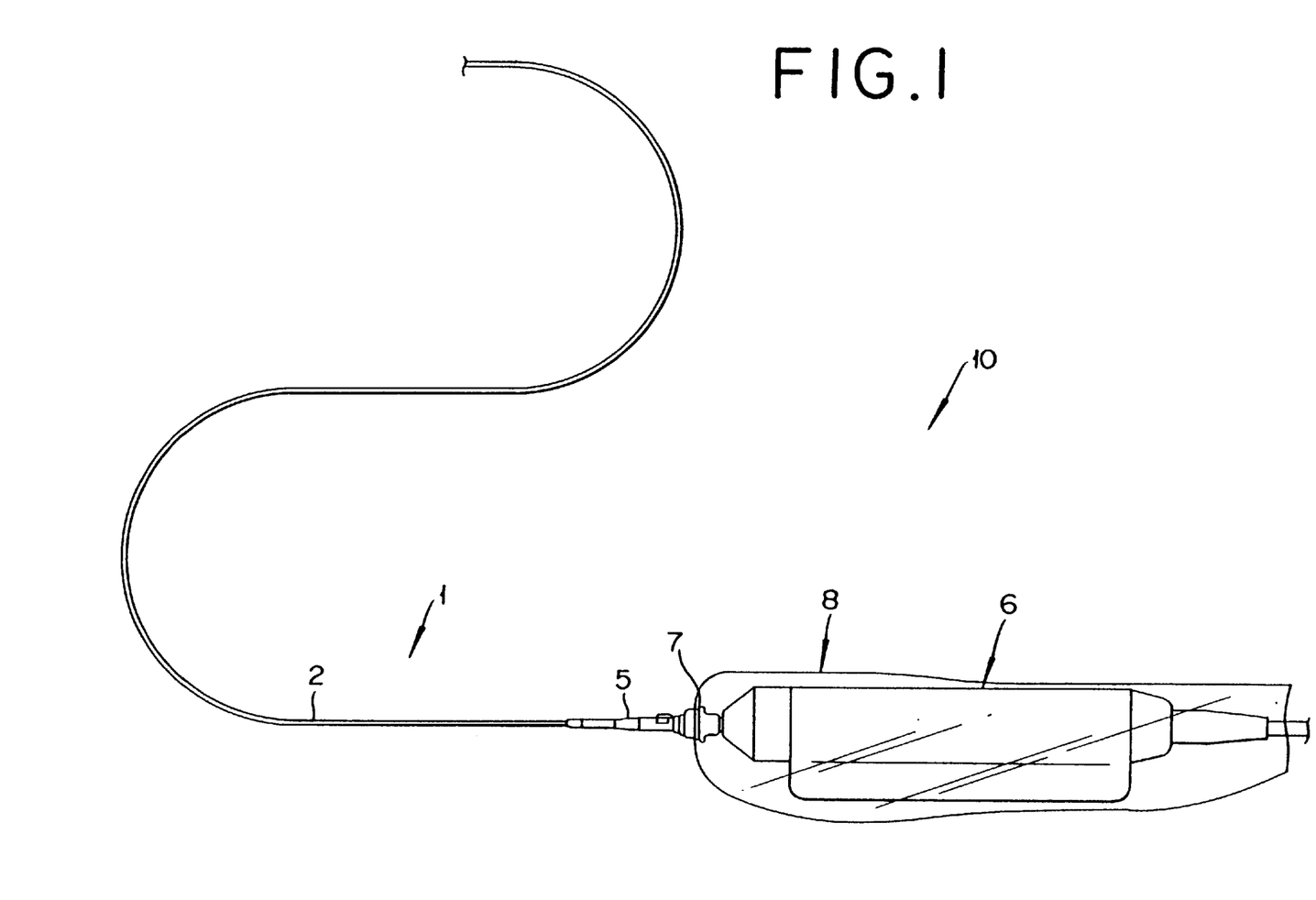
FIG. 1 is a whole side view illustrating an ultrasound imaging catheter system as the first preferred embodiment of this invention.

FIG. 1 is a whole side view illustrating an ultrasound imaging catheter system as the first preferred embodiment of this invention. An ultrasound imaging catheter system 10 illustrated in FIG. 1 comprises an ultrasound imaging catheter 1 as a tube unit provided with an inserting part to be inserted into the body cavity and a connector 5 disposed at the trailing end part thereof, an external drive device 6 as an external unit, an adapter 7, and a sterilized bag 8. Then, the inserting part mentioned above comprises a sheath 2 as an external tube, a drive shaft (not shown) inserted in the sheath 2 and adapted to transmit a mechanical driving force from the basal end side to the leading end side, and an ultrasound transducer (not shown) fixed at the leading end part of the drive shaft.

Figure 2:
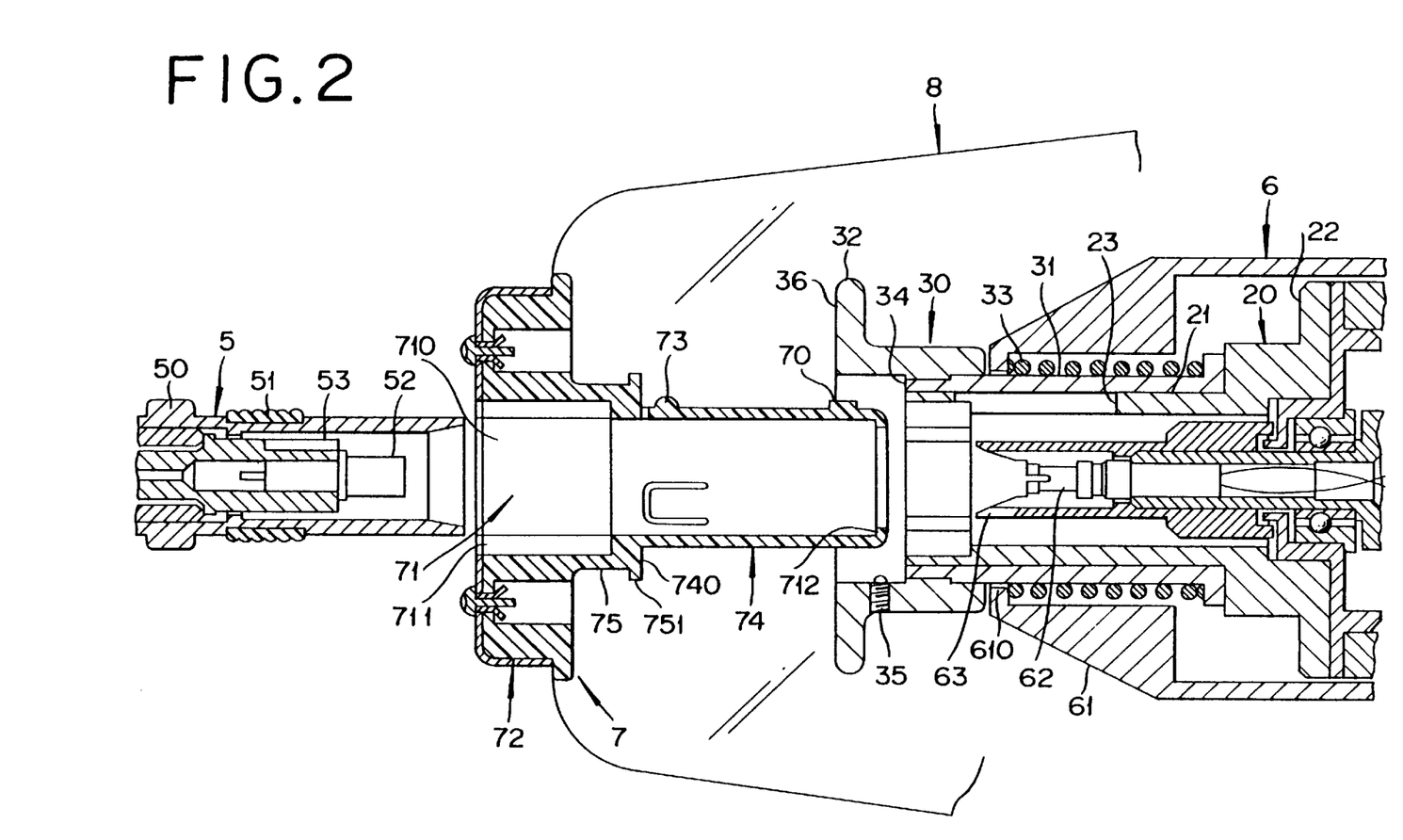
FIG. 2 is a cross section illustrating in a disassembled state the essential part of connected parts of the ultrasound imaging catheter shown in FIG. 1 and an external drive device.

FIG. 2 is a cross section illustrating in a disassembled state the essential part of connected parts of the ultrasound imaging catheter shown in FIG. 1 and an external drive device. On the connector 5, a pair of keys 50 are integrally formed in such a manner as to protrude from the outer peripheral part thereof and an insulator 51 formed of an elastomer such as, for example, natural rubber or synthetic resin and vested with elasticity is disposed on the outer peripheral part thereof as illustrated in FIG. 2. Further, inside the connector 5, a female electric contact point 52 and a connector side mechanical joint 53 are coaxially and rotatably mounted.

The external drive device 6 is provided with a motor (not shown) for rotating the drive shaft mentioned above and a connecting part 20 for removably connecting the connector 5 of the catheter 1 and the adapter 7. This connecting part 20 is provided therein with a male electric contact point 62 and an external drive device side mechanical joint 63.

Figure 3:
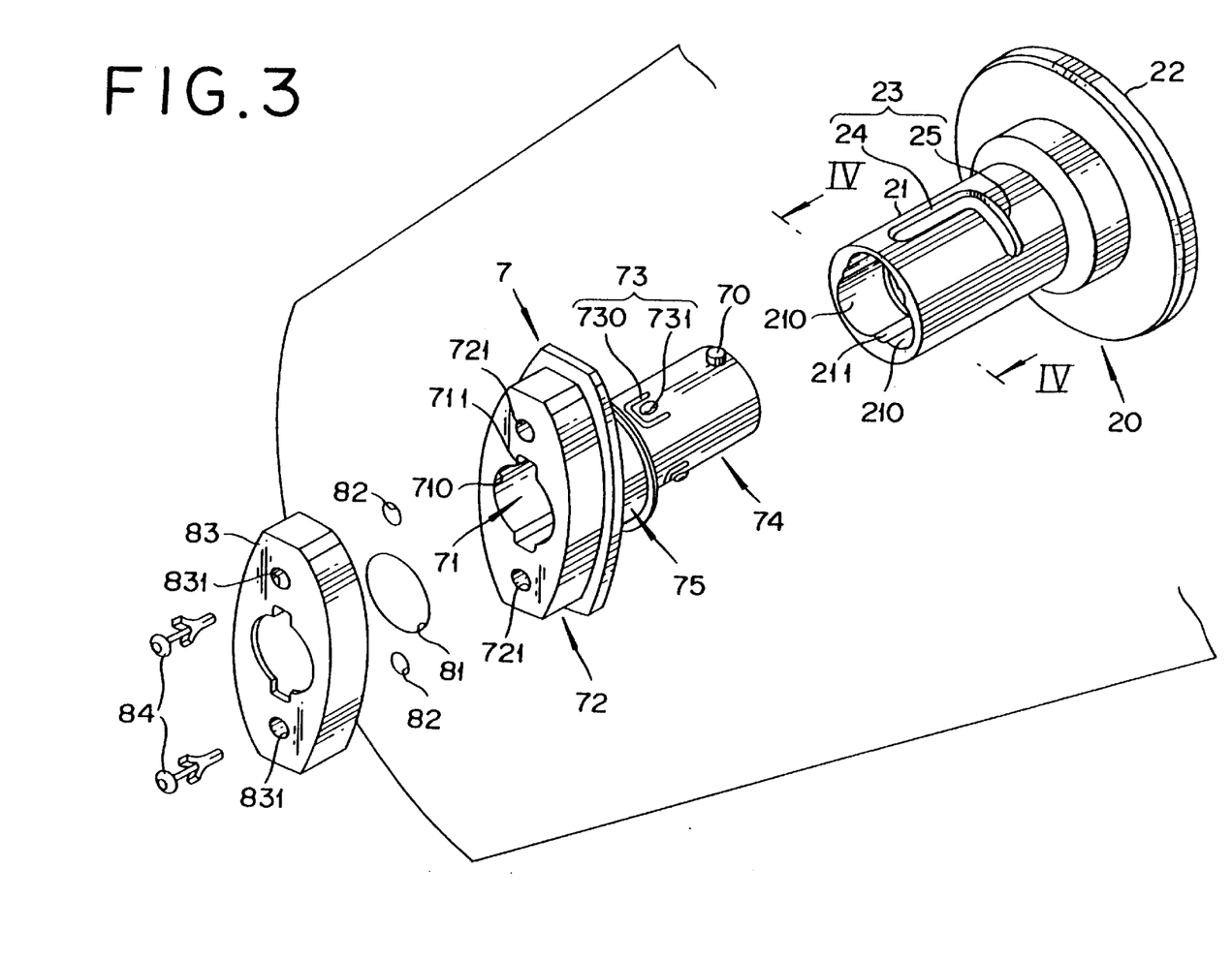
FIG. 3 is a perspective view illustrating in a disassembled state a connecting part of the external drive device, an adapter, a sterilized bag, and a cap shown in FIG. 2.

FIG. 3 is a perspective view illustrating in a disassembled state the connecting part of the external drive device, adapter, sterilized bag, and cap shown in FIG. 2. The connecting part 20, as illustrated in FIG. 3, is provided with a tubular part 21 assuming a substantially tubular shape and a flange part 22 formed at the terminal part of the tubular part 21. On the outer peripheral part of the hollow tubular part 21 of the connecting part 20, a cam groove 23 of a shape closely similar to the letter L and formed of an axial direction part 24 and a peripheral direction part 25 is formed. A protuberance 70 which will be specifically described herein below is adapted to be moved along the cam groove 23.

Figure 4:
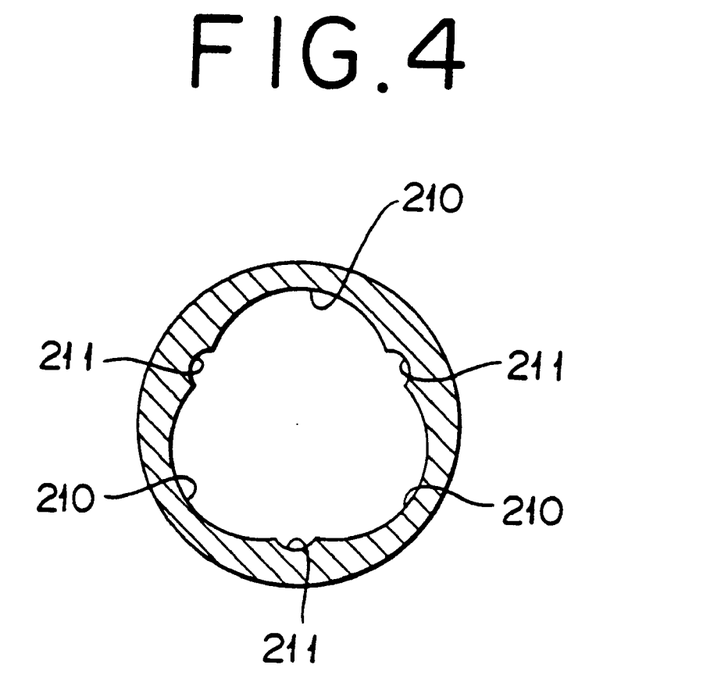
FIG. 4 is a cross section taken through FIG. 3 along the line IV—IV.

FIG. 4 is a cross section taken through FIG. 3 along the line IV—IV. Large-diameter parts 210 and small-diameter parts 211 are alternately formed three each on the circumference on the inner side at the catheter side leading end of the tubular part 21 of the connecting part 20 as illustrated in FIG. 4.

On the outer peripheral side of the connecting part 20, a slide member 30 is mounted slidably in the axial direction as illustrated in FIG. 2. This slide member 30 is provided with a tubular part 31 contacting the outer peripheral part of the connecting part 20, a finger grip part 32 fixed to one end of the tubular part 31, and a spring 33 for urging the slide member 30 toward the flange part 22 of the connecting part 20. On the lateral side of the tubular part 31, a fixing member 35 formed of a ball plunger is screwed in the radial direction. This fixing member 35 is provided with a tubular body having a male thread formed on the outer peripheral surface thereof, a ball retained inside the tubular body in such a manner as to attain protrusion over a prescribed distance from the leading edge thereof, and a spring member for urging the ball toward the leading end of the tubular body.

The adapter 7 is integrally composed of an insertion hole part 71 for allowing insertion of a connector therein, a handle part 72, an insertion shaft part 74 for insertion into the drive device, and a neck part 75. This insertion shaft part 74 assumes a tubular shape. In this insertion shaft part, the protuberance 70 and the lock part 73 mentioned above are integrally formed. A flange part 751 is formed on the insertion shaft part 74 side of the neck part 75. This flange part 751 has a structure such that it may be interlocked between the fixing member 35 and an end face 34 of the tubular part 31.

The insertion hole part 71 is provided with an insertion hole 710, a key groove 711, and an engaging part 712 and is adapted to admit the basal end side of the connector 5 of the ultrasound imaging catheter 1. The connector 5 is led in through the insertion hole 710 so as to ensure conformity of the key 50 thereof with the key groove 711 and is driven in as far as the engaging part 712.

The handle part 72 is formed in a noncircular cross section such as a starlike cross section or a roughly elliptic cross section such that the operator may take easy grip thereof. By moving the protuberance 70 along the cam groove 23 by means of this handle part 72, the adapter 7 in its entirely is enabled to be rotated easily and moved in the axial direction easily.

The lock parts 73, in the present embodiment, are formed one each at three places on the circumference 3. They each comprise a one-side flap 730 and a roughly spherically shaped projecting part 731 thrust toward the outside of the insertion shaft part 74. The flaps are formed in the same direction.

The adapter 7 is so constructed that when the insertion shaft part 74 of the adapter 7 is inserted into the connecting part 20 of the external drive device 6, the top part of the lock part 73 of the adapter 7 is positioned more on the inner side than the large-diameter part 210 of the tubular part 21 of the connecting part 20 and more on the outer side than the small-diameter part 211 and, as a result, the protuberance 731 is depressed by the small-diameter part 211. The inner surface of the small-diameter part 211 has a concave cross section approximately conforming in radius of curvature with the outer surface of the protuberance 731. The top part of the protuberance 70 of the adapter 7 is likewise so formed as to be positioned more on the inner side than the large-diameter part 210 of the tubular part 21 of the connecting part 20. Owing to the provision of the groove in the top part of the large-diameter part 210, the top part of the protuberance 70 is allowed to become larger on the outer side than the large-diameter part 210.

The lock part 73 enables the connector 5 of the ultrasound imaging catheter 1 to contact intimately the adapter 7 and the connecting part 20 and consequently prevents the vibration generated by the exertion of the drive torque on the external drive device 6 from being transmitted to the ultrasound imaging catheter 1. As a result, the ultrasound imaging catheter 1 is improved in performance and the operator is enabled to relieve the feeling of discomfort and fatigue.

The sterilized bag 8 is a preliminarily sterilized slender bag made of a transparent or translucent polymer such as, for example, vinyl chloride or polyethylene. It has a hole 81 of a small diameter formed in the terminal end, namely on the bottom side, thereof for the purpose of permitting insertion of the connector 5 therethrough. After a cap 83 has been used in conjunction with the adapter 7 to have the terminal end side of the sterilized bag 8 nipped therebetween, rivets 84 are inserted through fitting holes 831, 721, and 82 and fixed. The rivets 84 are only required to be such that when they are driven home, the leading end parts thereof may be spread out and enabled to fix the cap 83 and the adapter 7. By connecting the sterilized bag 8 integrally or removably to the adapter 7 as described above, the situation that the external drive device accidentally smears the catheter or the operator's hand can be infallibly prevented.

A cover 61 of the external drive device 6 is provided with a small-diameter part 610 and consequently enabled to retain the spring 33 inside the external drive device 6.

Now, the method for operating the ultrasound imaging catheter system 10 according to this invention and the function thereof will be described.

For a start, the system is to be prepared for the operation. First, the external drive device 6 is wholly inserted in the sterilized bag 8 to which the adapter 7 is fitted by the use of the cap 83 and the rivets 84. The adapter 7, the cap 83, the rivets 84 and the sterilized bag 8 are used herein as nearly sterilized (or perfectly sterilized occasionally). Then, the adapter 7 is pushed in so that the protuberance 70 thereof may be laid along the longitudinal direction of the axial direction part 24 of the cam groove 23 formed in the connecting part 20 of the external drive device 6.

Figure 5:
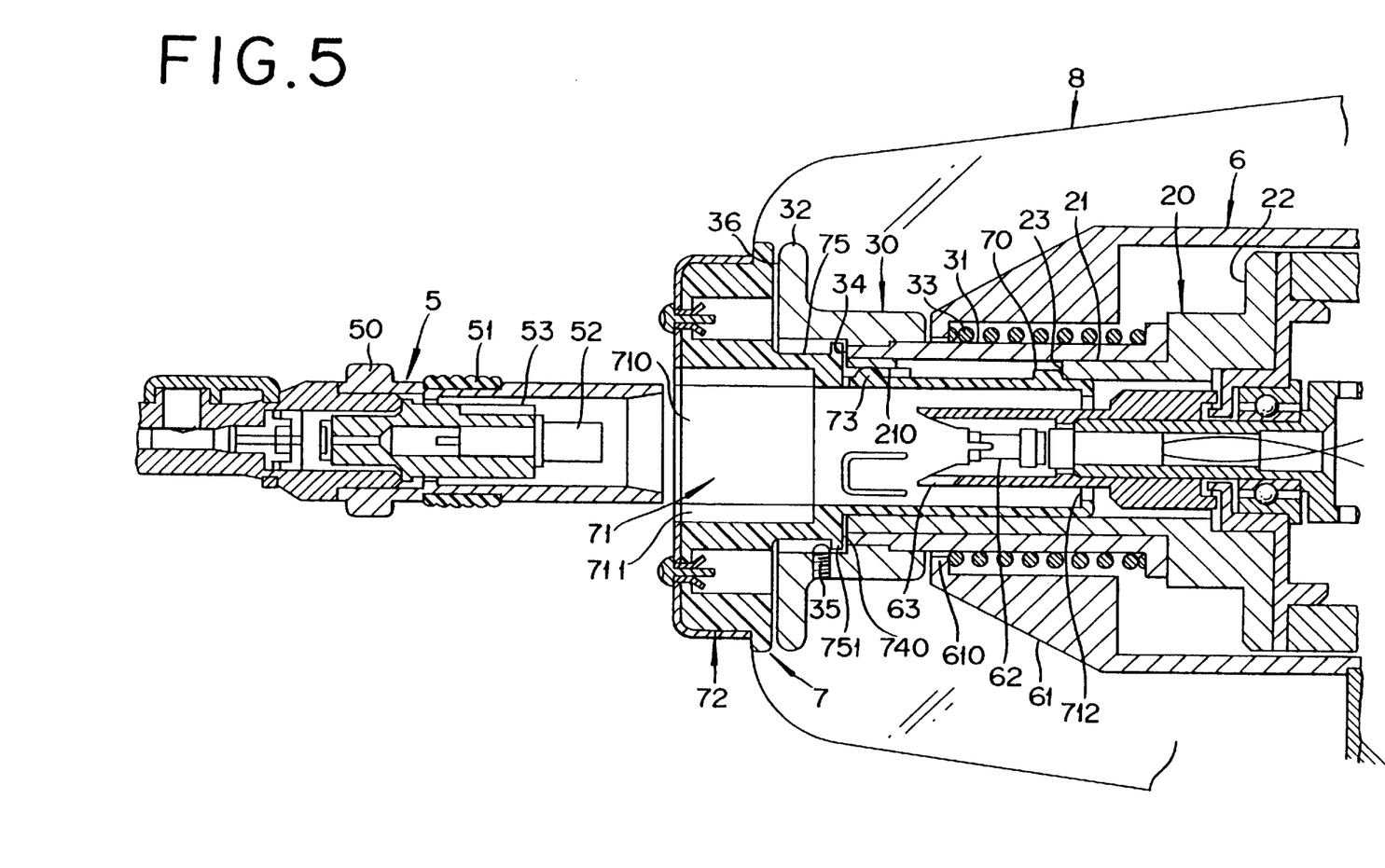
FIG. 5 is a cross section illustrating the state in which an adapter is inserted into the connecting part of the external drive device.
Figure 7A:
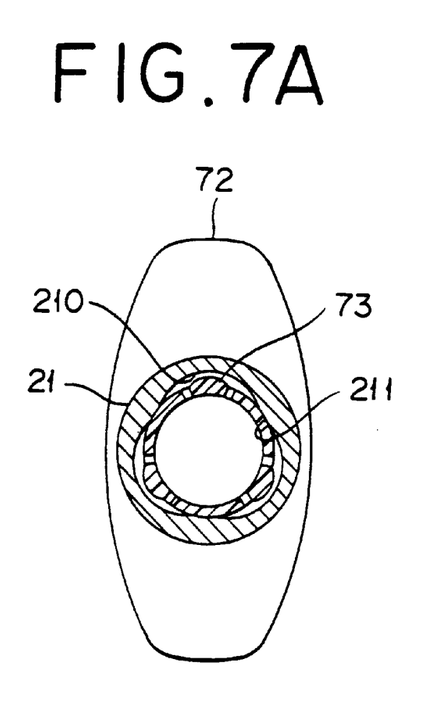
FIG. 7A–FIG. 7C are cross sections intended as specimens to aid in describing the manner in which a flap of a lock part is gradually deforming toward the inside diameter in consequence of the rotation of the adapter.

The adapter 7, with the flange part 751 thereof forcing the ball of the fixing member 35 backward toward the exterior, is pushed in until a seating surface 740 formed on the adapter collides or verges on colliding with the end face 34 of the tubular part 31 of the sliding member 30 as illustrated in FIG. 5. When the flange part 751 is pushed in to this position, the ball of the fixing member 35 is returned by the force of a spring and caused to fix the adapter 7. Thus, the adapter 7 is inserted into the connecting part 20 of the external drive device 6 and, by the fact that the flange part 751 is interlocked between the fixing member 35 and the end face 34 of the tubular part 31, is fixed with proper retaining power. At this time, the protuberance 70 of the adapter 7 is positioned exactly at the end part in the longitudinal direction of the axial direction part 24 of the cam groove 23. It is permissible to keep the adapter 7 and the sterilized bag 8 separated initially and cause them to join at this time. The positioning completes the preparation. Incidentally, at this time, the protuberance 731 of the adapter 7 is at such a position that it may neither touch the inner surface of the large-diameter part 210 formed at the entrance to the connecting part 20 or nor succumb to the depressing force exerted by the large-diameter part 210 (FIG. 5 and FIG. 7A refer).

Figure 6:
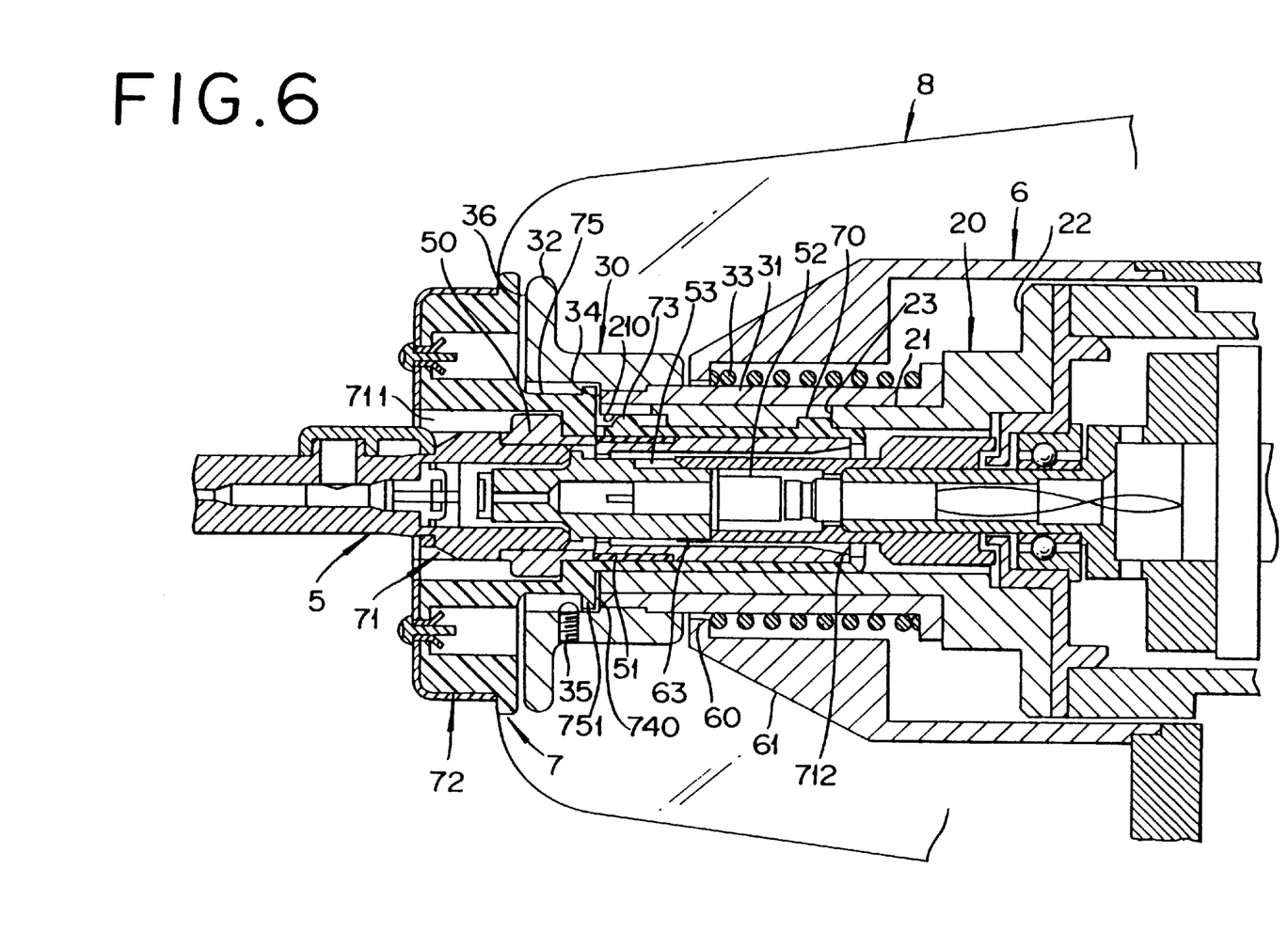
FIG. 6 is a cross section illustrating the state in which he connector of the catheter is inserted through the medium of the adapter into the external drive device.

Subsequently, the connector 5 of the ultrasound imaging catheter 1 is inserted, with the key 50 kept in alignment with the key groove 711, into the insertion hole part 71 of the adapter 7 as far as the engaging part 712 as illustrated in FIG. 6. At this time, the inner face of the flap 730 of the lock part 73 is positioned just the outer side of the insulator 51 of the connector 5. Immediately before this time, the female electric contact point 52 of the connector 5 and the male electric contact point 62 of the external drive device contact each other and the mechanical joints 53 and 63 thereof establish mechanical contact.

Since the diameter of the insulator 51 is slightly smaller than the inside diameter of the insertion hole 710, the insulator 51 and the insertion hole 710 remain in light contact with each other. Thus, the connector and the adapter 7 in the state illustrated in FIG. 6 can be easily released and coupled.

Figure 7B:
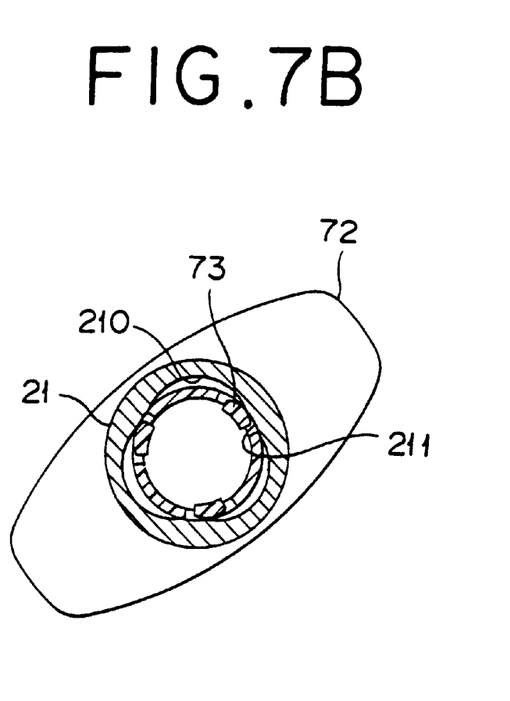

Then, to connect and fix the connector 5 of the ultrasound imaging catheter 1, the handle part 72 of the adapter 7, as held in the state illustrated in FIG. 6, is rotated by 45 degrees clockwise in the direction of the external drive device 6. At this time, the protuberance 70 is moved along the peripheral direction part 25 of the cam groove 23 till the end part of the groove. The connector 5 rotates under slight contact pressure in conjunction with the adapter 7. Gradually, the protuberance 731 collides with the small-diameter part 211 formed at the entrance to the connecting part 20 and the flap 730 begins bending toward the inner side of the adapter 7. As a result, the inner face of the flap 730 begins encroaching on the insulator 51 (FIG. 7B refers). The angle of rotation in this case is preferred to be in the range of 30 degrees–90 degrees. If this angle is unduly large, the excess will possibly twist the bag and inflict breakage thereon.

Figure 7C:
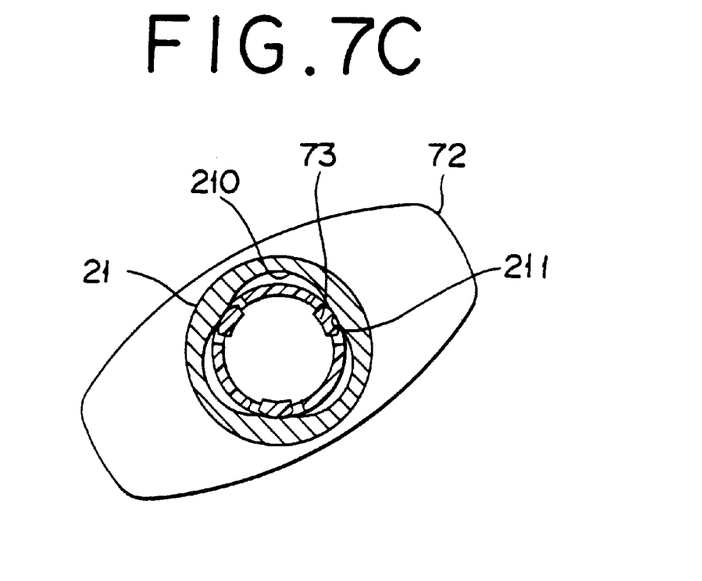
Figure 8:
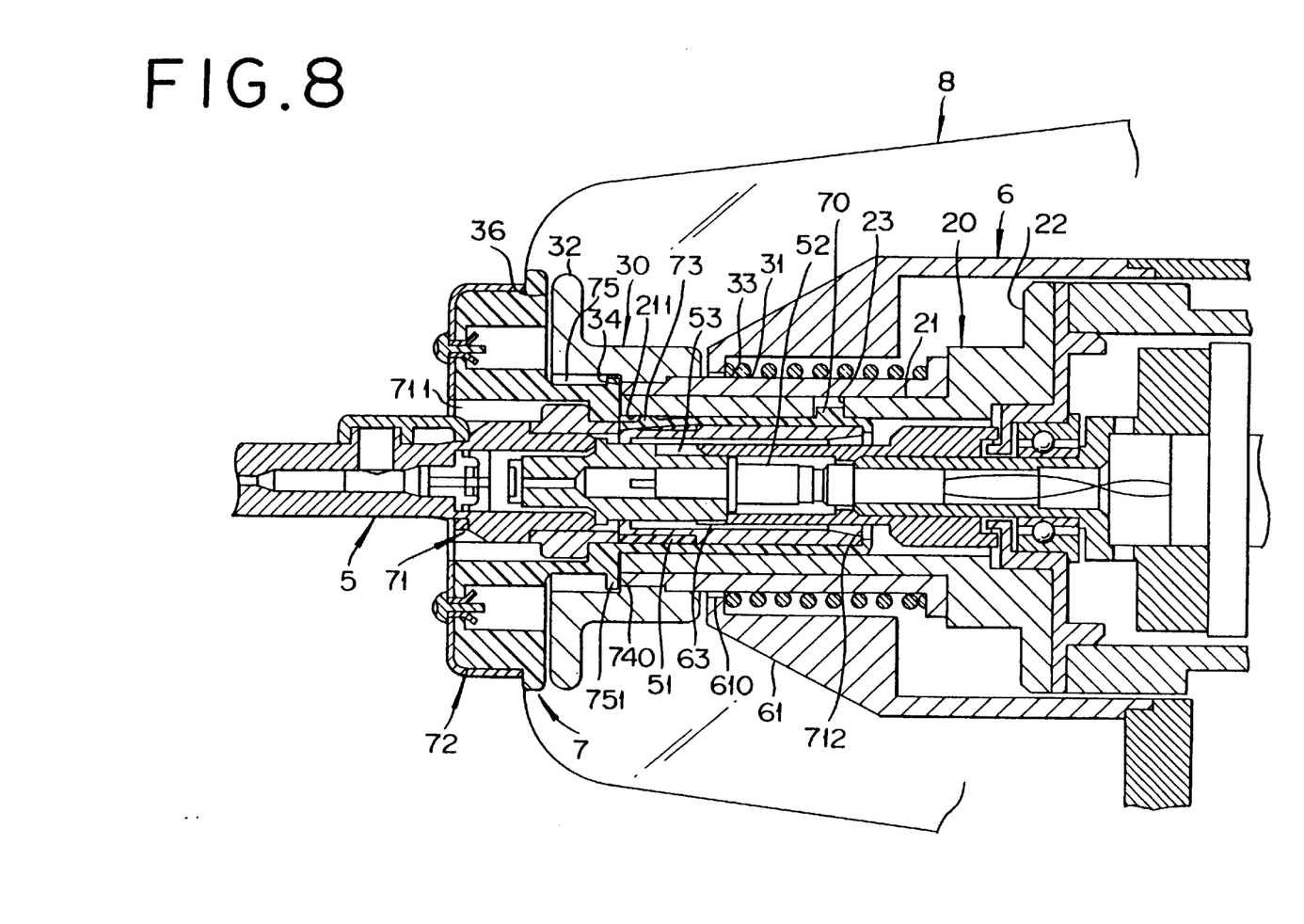
FIG. 8 is a cross section illustrating the state in which the connector and the adapter are perfectly fixed in tight adhesion by the lock part.

When the protuberance 731 of the lock part 73 almost reaches the center of the small-diameter part 211 as illustrated in FIG. 8, the connector 5 is completely fixed by the flap 730 in intimate contact with the adapter 7 (FIG. 7C and FIG. 8 refer).

The adapter 7 and the connecting part 20 are clamped with even force in three directions by the protuberance 731. And they are prevented from wavering. They are, however, allowed to move in the axial direction (excepting when the protuberance 70 is positioned inside the peripheral direction part 25 of the cam groove 23) or to move in the circumferential direction because at least either of them is formed of a material with a low coefficient of sliding friction (such as, for example, polyphenylenesulfide, polyacetal or tetrafluoroethylene resin, optionally reinforced with glass fibers).

The ultrasound imaging catheter 1 is set operating when the motor of the external drive device 6 in the ensuant state is actuated.

Now, the method for withdrawing the ultrasound imaging catheter 1 from the external drive device 6 will be described below.

The motor of the external drive device 6 is stopped and the handle part 72 of the adapter 7 is rotated counterclockwise in the direction of the external drive device 6. The protuberance 70 of the adapter 7 is moved along the peripheral direction part 25 of the cam groove 23 from the end part of the groove to the intersection with the axial direction part 24. Since the protuberance 731 is thus moved to the position opposite the inner face of the large-diameter part 210 formed at the entrance to the connecting part 20, the flap 730 is returned to the home position and relieved of the state locked to the connector 5 (in the state illustrated in FIG. 6).

Subsequently, the finger grip part 32 of the slide member 30 is moved toward the catheter against the urging force of the spring 33. As a result, the end face 34 of the slide member 30 or the end face 36 of the finger grip part 32 evenly depresses the adapter 7 and the adapter 7 is moved in conjunction with the connector 5 toward the catheter. At the same time, the electric contact and the mechanical contact are broken. At this time, the ultrasound imaging catheter 1 can be easily withdrawn from the adapter 7. Incidentally, the adapter 7 escapes this release owing to the fixing member 35.

The connector 5, as surmised from the construction described above, is exposed to unsterilized parts (the male electric contact point 62 of the external drive device 6 and the mechanical joint 63) in the interior thereof. Since the connector 5 has a sufficiently small opening part and is positioned in deep recess from the opening part, the possibility of the operator touching a contaminated part is nil even when the connector 5 is once connected to the external drive device 6 and then made to release it. So long as the adapter 7 is sterilized, therefore, the sterilized state of the ultrasound imaging catheter 1 can be retained even when the connector is connected again to the external drive device 6 through the medium of the adapter 7. As a result, the ultrasound imaging catheter can be released from or coupled with the external drive device while the catheter system is in use. At various steps of the operation of the catheter, therefore, the joints between the ultrasound imaging catheter and the external drive device can avoid the situation of exposing themselves to an external attack, with the result that the ultrasound imaging catheter will be prevented from breakage. After the confirmation of the operation of the catheter, the connector of the catheter may be removed from the external drive device without interrupting the catheter operation.

Figure 9:
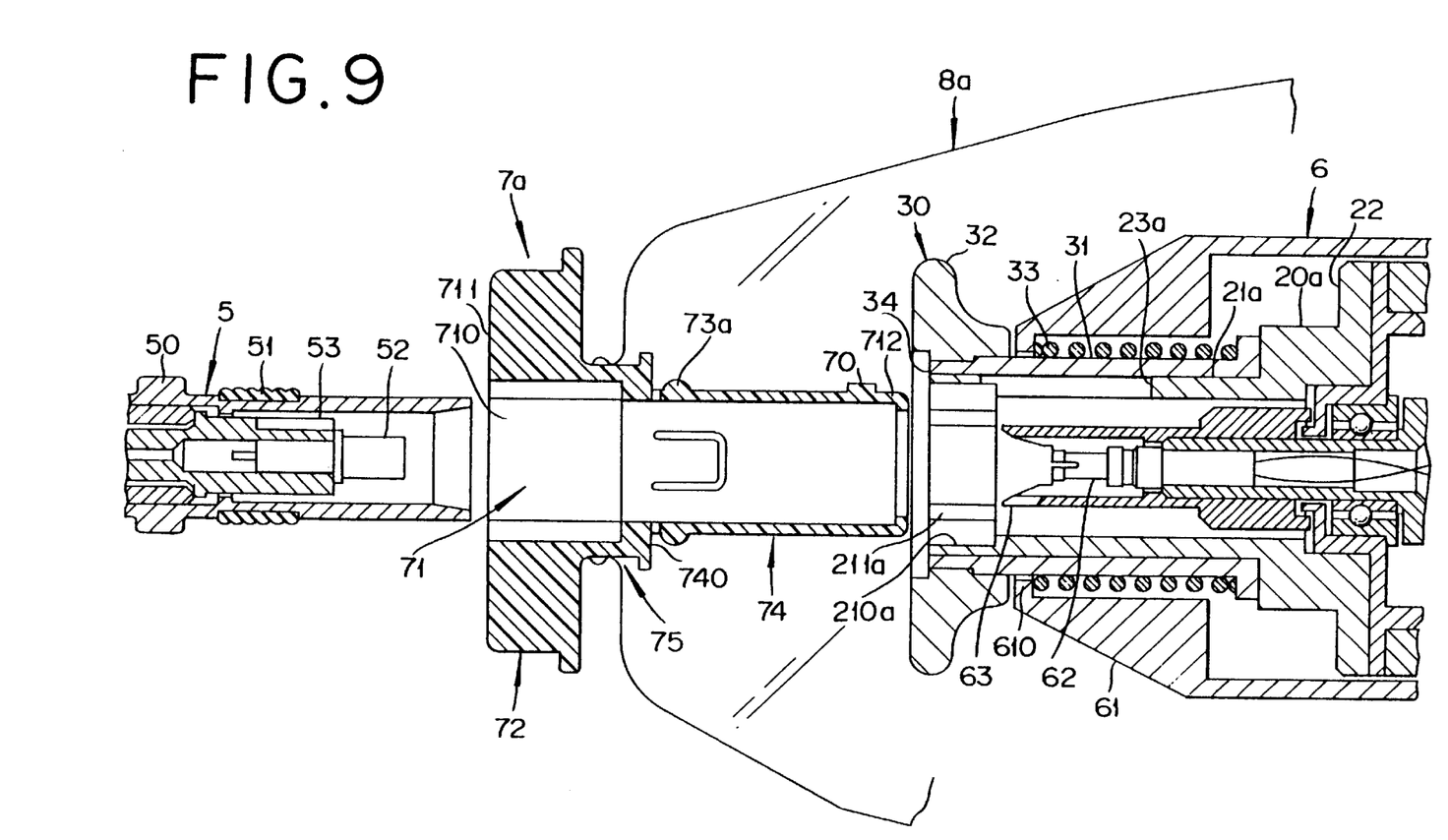
FIG. 9 is a cross section illustrating in a disassembled state the essential part of connected parts of an ultrasound imaging catheter of an ultrasound imaging catheter system as the second embodiment of this invention and the external drive device.
Figure 10:
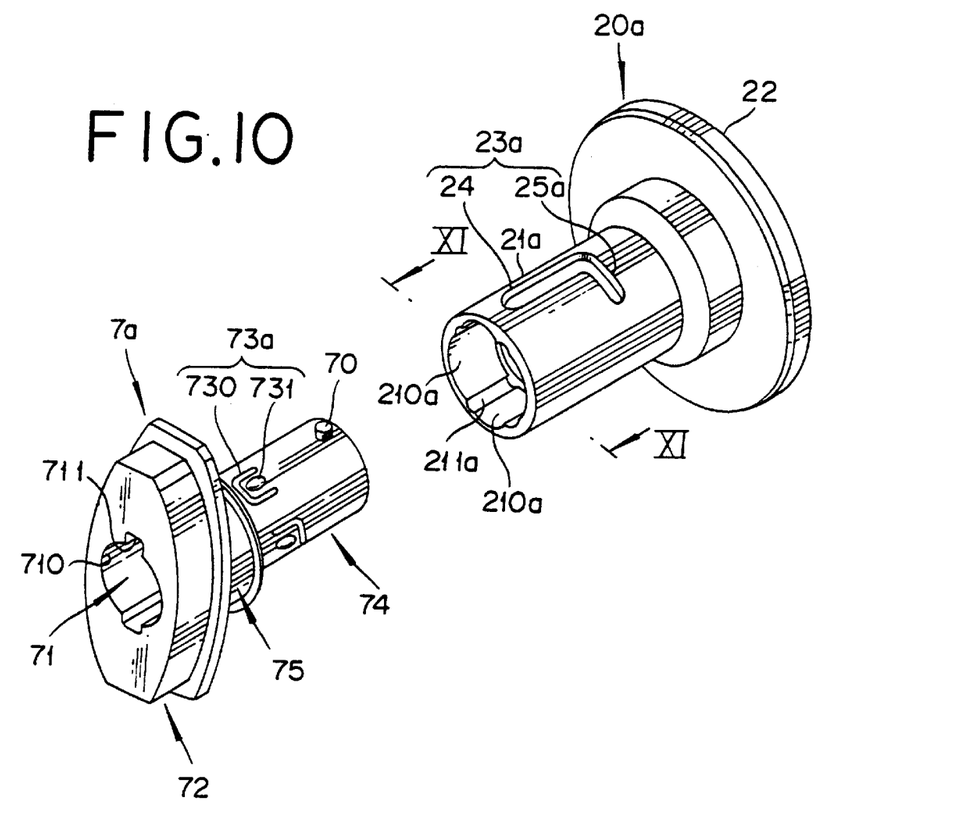
FIG. 10 is a perspective view illustrating in a disassembled state a connecting part of the external drive device and an adapter shown in FIG. 9.
Figure 11:
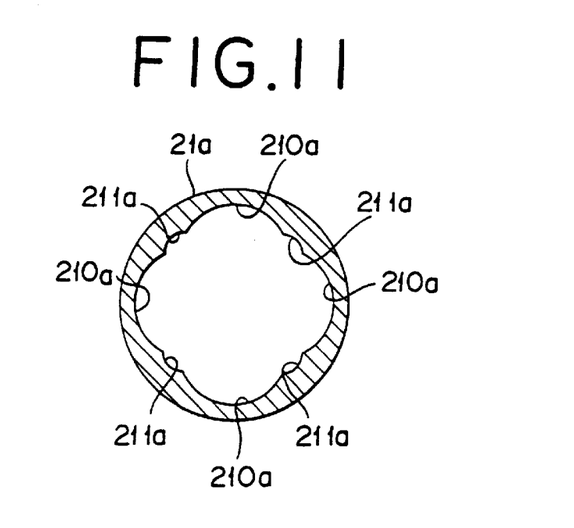
FIG. 11 is a cross section taken through FIG. 10 along the line XI—XI.

FIG. 9 is a cross section illustrating in a disassembled state the essential part of the connecting part of the ultrasound imaging catheter and the external drive device in the ultrasound imaging catheter system as the second embodiment of this invention, FIG. 10 is a perspective view illustrating in a disassembled state the connecting part of the external drive device and the adapter shown in FIG. 9, and FIG. 11 is a cross section taken through FIG. 10 along the line XI—XI.

In the second embodiment, one hole is opened at the terminal end, namely on the bottom side, of a sterilized bag 8a. Then, the sterilized bag 8a can be easily fitted to an adapter 7a by inserting the neck part 75 of the adapter 7a into the hole on the terminal end side of the sterilized bag 8 and fixing it to the bag with a rubber band or a double-face adhesive tape.

The lock parts 73a of the adapter 7a are formed one each at four places on the circumference and the flaps 730 thereof have their directions changed alternately so as to preclude otherwise possible deterioration of rigidity (FIG. 10 refers). On the inner side of the catheter side leading end of a tubular part 21a of a connecting part 20a, large-diameter 210a and small-diameter parts 211a are alternately formed each at four places on the circumference. Then, on the outer peripheral part of the tubular part 21a, a cam groove 23a of a shape closely similar to the letter L and formed of an axial direction part 24 and a peripheral direction part 25a is formed. The peripheral direction part 25a is formed in the range of about 45 degrees on the circumferential direction.

Incidentally, the cam groove 23 of the connecting part 20a and the protuberance 70 of the adapter 7a are integrally formed so as to be symmetrized also in the diametric direction. They are omitted from the diagram for the sake of simplicity.

Since the second embodiment is identical with the first embodiment described above, like parts are denoted by like reference numerals and are omitted from the following description.

Figure 12:
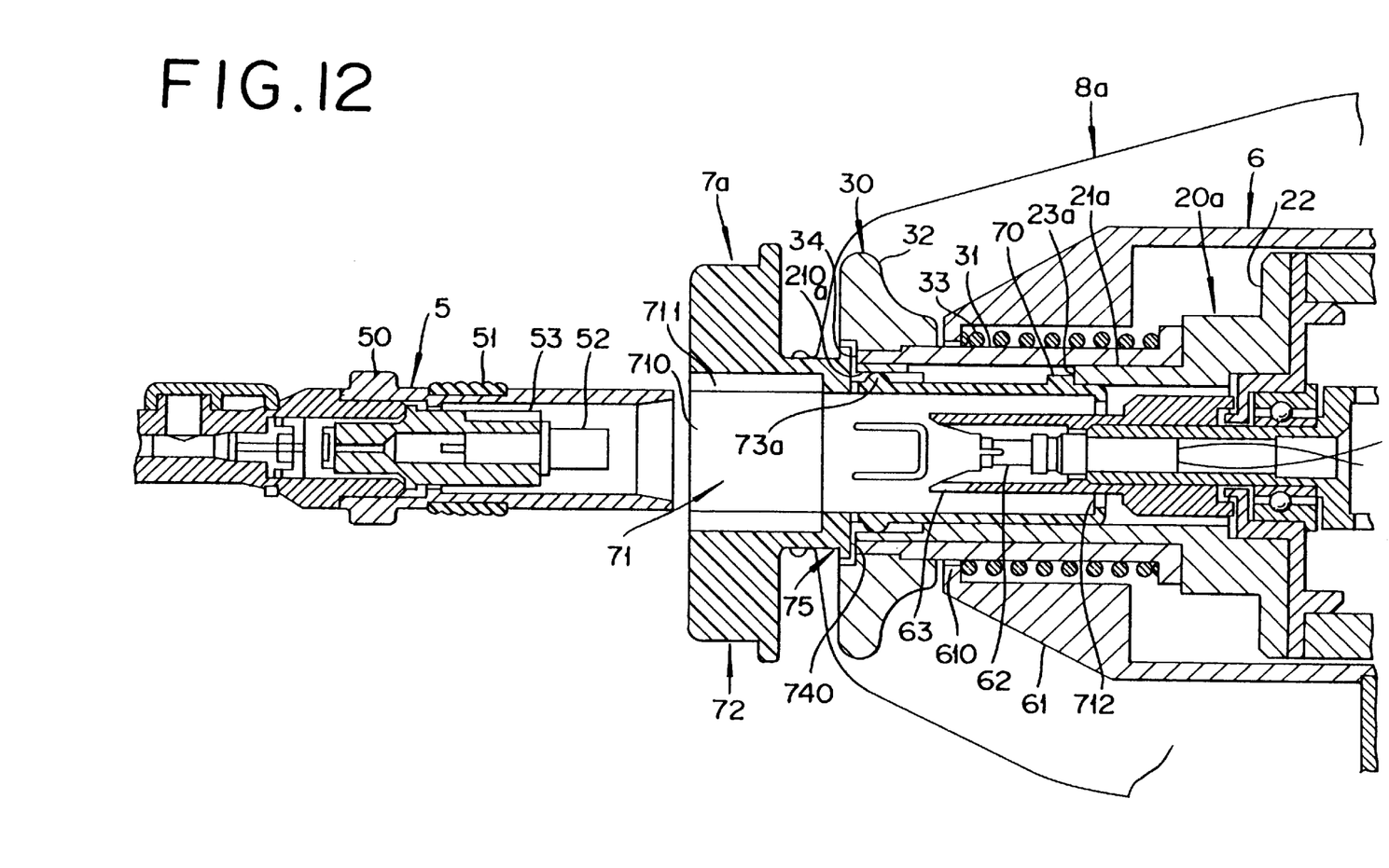
FIG. 12 is a cross section illustrating the state in which the adapter is inserted into the connecting part of the external drive device.

The present ultrasound imaging catheter system is operated in almost the same manner as in that of the first embodiment described above. FIG. 12 is a cross section illustrating the state in which the adapter is inserted into the connecting part of the external drive device, FIG. 13 is a cross section illustrating the state in which the connector of the catheter is inserted through the medium of the adapter into the external drive device, FIG. 14A–FIG. 14C are specimen cross sections as aids in describing the manner in which the flaps of the lock part are gradually bent toward the inner side in consequence of the rotation of the adapter, and FIG. 15 is a cross section illustrating the state in which the connector and the adapter are perfectly fixed in intimate contact by the lock part.

Figure 13:
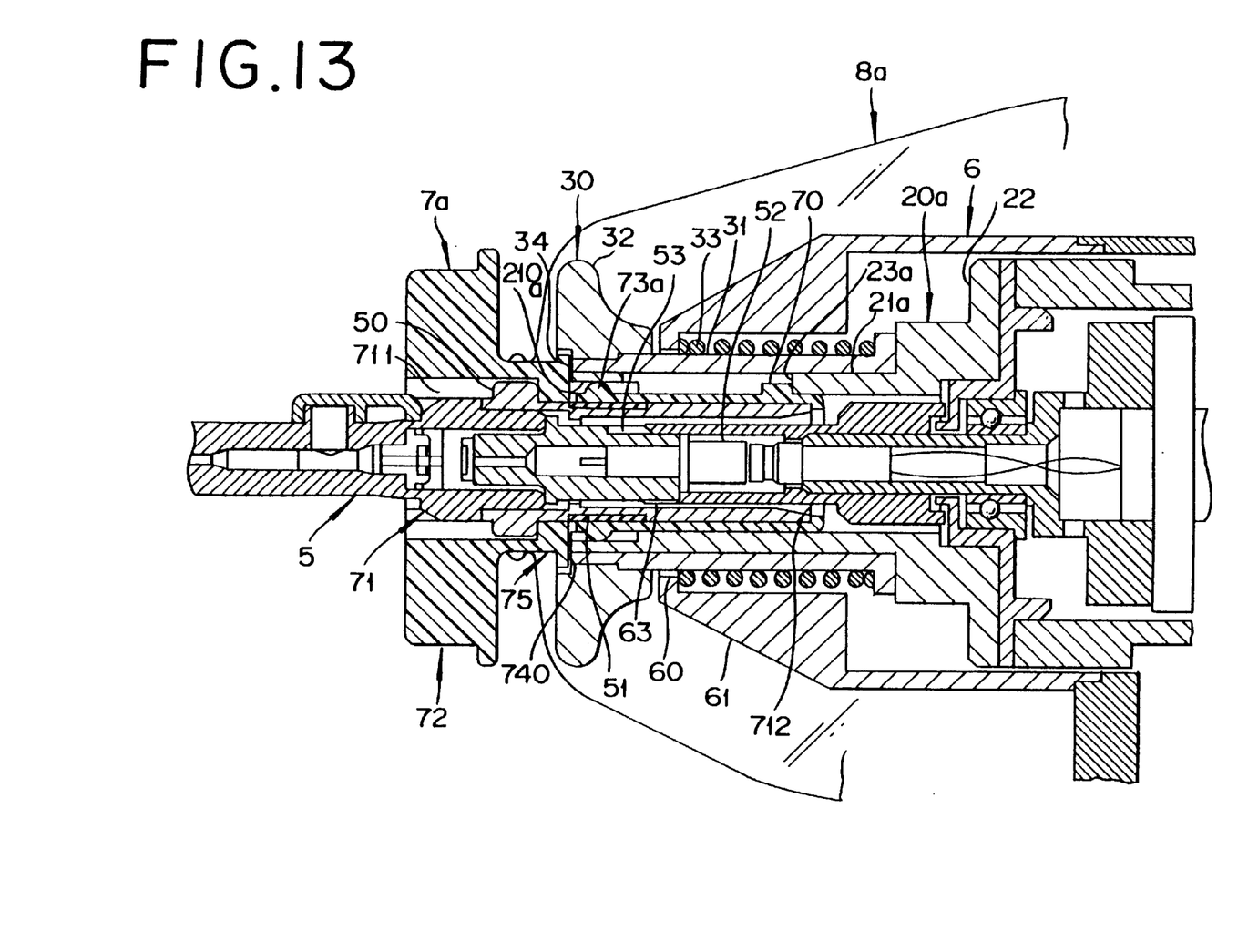
FIG. 13 is a cross section illustrating the state in which the connector of the catheter is connected through the medium of the adapter to the external drive device.
Figure 14A:
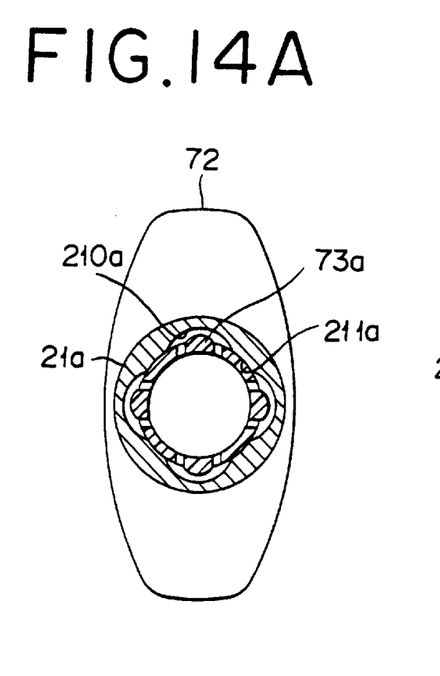
FIG. 14A–FIG. 14C are cross sections intended as specimens to aid in describing the manner in which the flap of the lock part is gradually deforming toward the inside diameter in consequence of the rotation of the adapter.
Figure 14B:
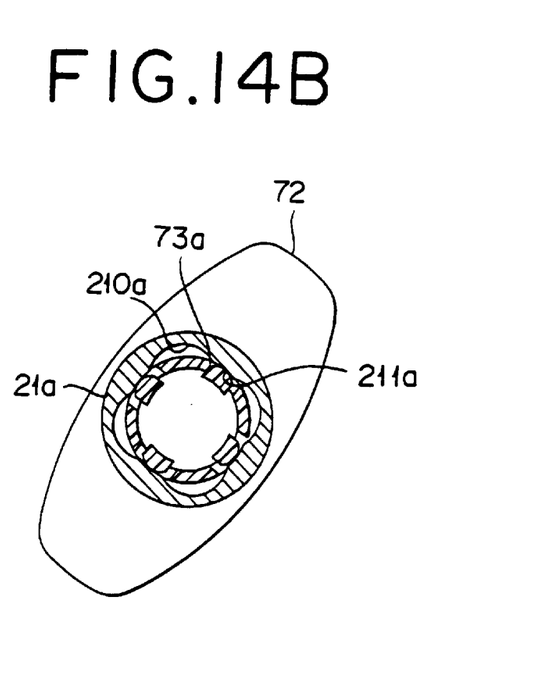
Figure 14C:
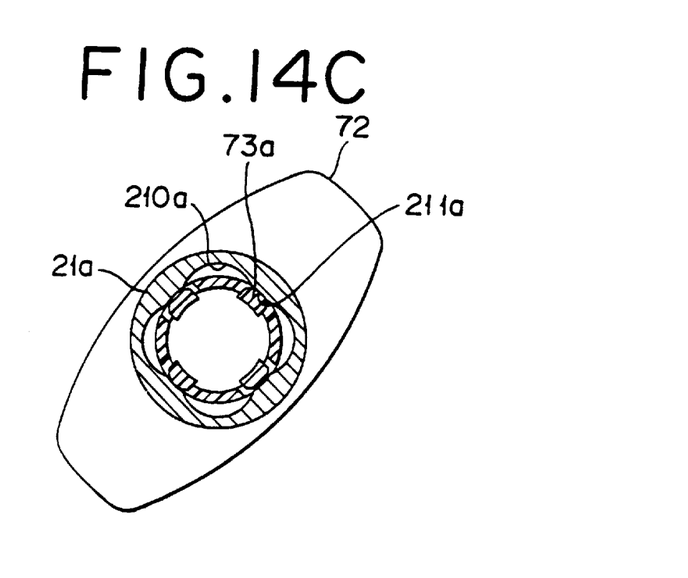
Figure 15:
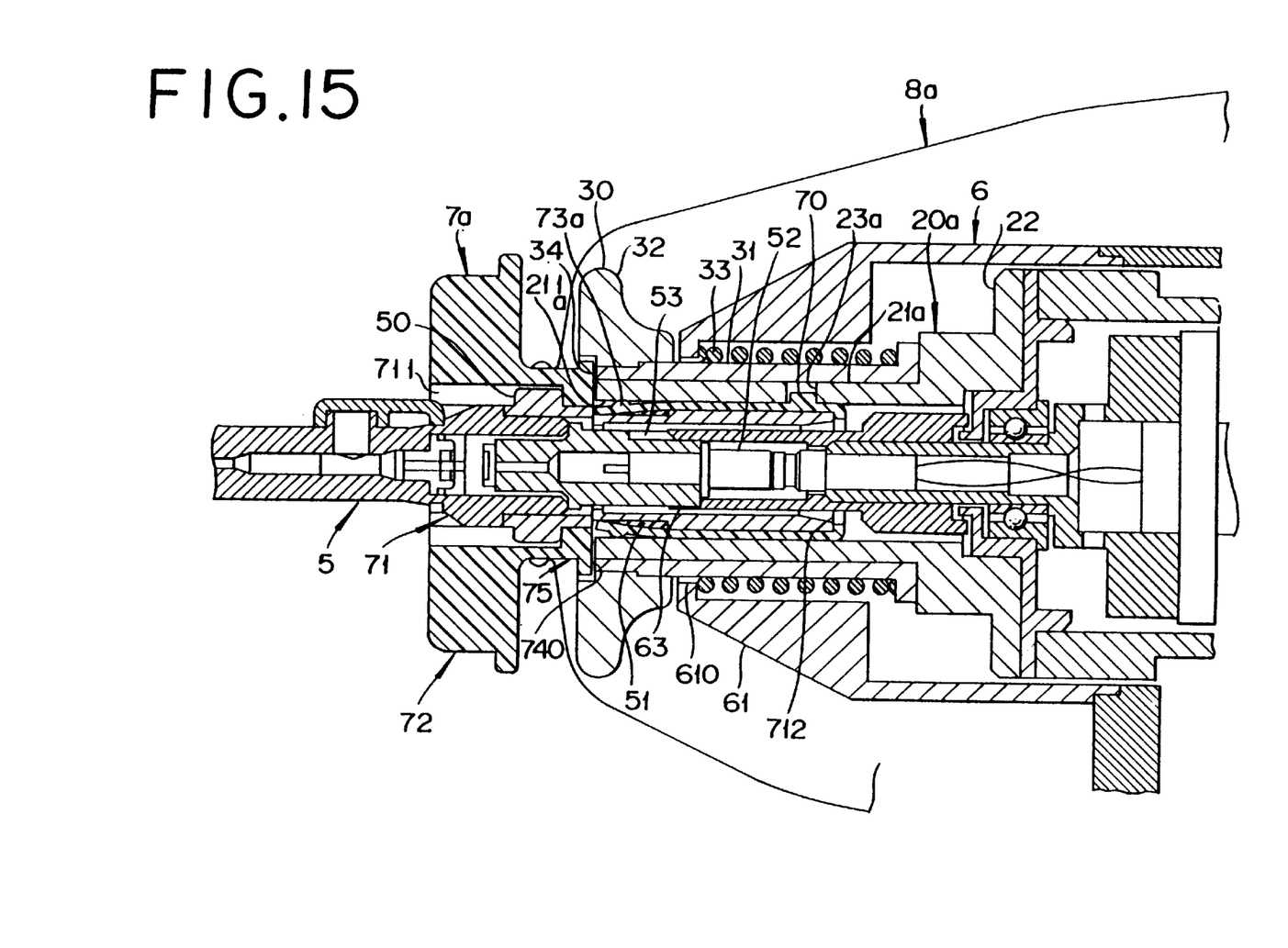
FIG. 15 is a cross section illustrating the state in which the connector and the adapter are perfectly fixed in tight adhesion by the lock part.

To put this ultrasound imaging catheter system to use, the adapter 7a is pushed in so as to move the protuberance 70 thereof along the longitudinal direction of the axial direction part 24 of the cam groove 23a formed in the connecting part 20a of the external drive device 6, the connector 5 of the ultrasound imaging catheter 1 is inserted into the insertion hole part 71 of the adapter 7a, and the handle part 72 of the adapter 7a is rotated from the state illustrated in FIG. 13 by 45 degrees clockwise in the direction of the external drive device 6 as illustrated in FIG. 14A–FIG. 14C. As a result, the adapter 7a and the connecting part 20a are clamped with even force in four directions by the protuberances 731.

Since the connector 5 and the external drive device 6 are likewise connected through the medium of the sterilized adapter 7a in accordance with the second embodiment, the part of the connector of the ultrasound imaging catheter can be prevented from contamination and consequently the ultrasound imaging catheter can retain the sterilized state thereof in the same manner as in the first embodiment described above. As a result, the ultrasound imaging catheter can be released from and coupled with the external drive device without interrupting the operation of the system, the insertion of the catheter into the blood vessel can be facilitated, and the ultrasound imaging catheter can be prevented from breakage.

It is obvious that this invention is not limited to the particular embodiments shown and described above but may be variously changed and modified without departing from the technical concept of this invention.

For example, the lock parts 73, 73*a* of the adapters 7, 7*a* may be provided one each at one place on the circumference. The rotation of the protuberances 70 along the peripheral direction parts 25, 25*a* of the cam grooves 23, 23*a* may be produced counterclockwise instead relative to the external drive device. The cam grooves 23, 23*a* do not need to have a shape closely similar to the letter L as mentioned above. The number of protuberances 70 of the adapters 7, 7*a* may be one or in a suitably selected plurality. The spring 33 may be omitted. The lock mechanism is arbitrarily selected so long as it serves as a means for pressing the lock parts 73, 73*a* fast against the connector 5. Optionally, it may be so constructed as to obviate the necessity for a cam groove.

If the ultrasound imaging catheter is not possessed of an electronic scan type rotary drive mechanism, for example, it tolerates the absence of such a lock mechanism as described above. The connector 5, the insertion hole part 71, the connecting part 20, etc. may not be in a tubular shape.

The embodiments, cited above, have depicted the ultrasound imaging catheter system. Optionally, this invention can be applied to the endoscope system, for example, which is intended to attain internal observation of the tubular cavity.

This application is based on Application No. 10-053564 filed in Japan, the contents of which are herein incorporated by way of reference.

What is claimed is:

1. A tube unit system comprising
   a tube unit provided with an insertion part possessing a tube to be inserted into a body cavity and a connector disposed on a handle side of the insertion part;
   an external unit provided with a connecting part to be connected to said connector of said tube unit; and
   an adapter having undergone a purifying treatment and adapted to be interposed between said connector and said connecting part; said adapter being attachable to and detachable from said connector and said connecting part, wherein said adapter has integrally or removably connected thereto a bag serving to cover said external unit and having undergone a purifying treatment.

2. The tube unit system according to claim 1, wherein said tube unit is provided with a drive shaft disposed inside said tube and serving to transmit a mechanical driving force from a basal end side to a leading end side, and said external unit is provided with a motor for rotating said drive shaft.

3. A tube unit system according to claim 2, wherein said adapter is provided with a lock means for tightly fixing said connector and said connecting part to each other.

4. A method for observing an interior of a body cavity with an ultrasound imaging catheter, comprising
   covering an external drive device for driving said ultrasound imaging catheter with a bag having undergone a purifying treatment;
   connecting an adapter having undergone a purifying treatment to a connecting part of said external drive device;
   connecting a connector of said ultrasound imaging catheter having undergone such a purifying treatment through said adapter to said external drive device; and
   setting said external drive device into operation.

5. A tube unit system comprising
   a tube unit including an insertion part to be inserted into a person's body and a connector disposed at an end of the insertion part;
   an external unit provided with a connecting part connectable to said connector;
   a sterilized adapter adapted to be interposed between said connector and said connecting part, said adapter being attachable to and detachable from both said connector and said connecting part, said adapter being movable when attached to said connecting part to fix the connector relative to said connecting part; and
   a bag subjected to purifying treatment and connected to said adapter to cover said external unit.

6. The tube unit system according to claim 5, wherein said bag is removably connected to said adapter.

7. The tube unit system according to claim 5, wherein said bag is integrally connected to said adapter.

8. The tube unit system according to claim 5, wherein said adapter is provided with a lock means for tightly fixing said connector and said connecting part to each other.

9. The tube unit system according to claim 5, including a slide member slidably mounted on the connecting part of the external unit.

10. The tube unit system according to claim 5, wherein the connecting part of the external unit includes a tubular part having an inner periphery, and including at least one relatively smaller diameter portion and at least one relatively larger diameter portion.

11. A tube unit system comprising
    a tube unit including an insertion part to be inserted into a person's body and a connector disposed at an end of the insertion part;
    an external unit provided with a connecting part connectable to said connector;
    a sterilized adapter adapted to be interposed between said connector and said connecting part, said adapter being attachable to and detachable from both said connector and said connecting part, said adapter being movable when attached to said connecting part to fix the connector relative to said connecting part;
    a slide member slidably mounted on the connecting part of the external unit; and
    a spring operatively associated with said slide member to urge said slide member in a direction relative to said connecting part of the external unit.

12. A tube unit system comprising
    a tube unit including an insertion part to be inserted into a person's body and a connector disposed at an end of the insertion part;
    an external unit provided with a connecting part connectable to said connector; and
    a sterilized adapter adapted to be interposed between said connector and said connecting part, said adapter being attachable to and detachable from both said connector and said connecting part, said adapter being movable when attached to said connecting part to fix the connector relative to said connecting part, wherein the connector includes an electric contact point and the connecting part includes an electric contact point, the electric contact point of the connector contacting the electric contact point of the connecting part when the connecting part is connected to the connector.

* * * * *